(12) United States Patent
Fukumoto (10) Patent No.: US 11,789,283 B2
(45) Date of Patent: Oct. 17, 2023

(54) IMAGING APPARATUS (71) Applicant: CANON KABUSHIKI KAISHA, Tokyo (JP)

(72) Inventor: Junya Fukumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 429 days.

(21) Appl. No.: 16/988,893

(22) Filed: Aug. 10, 2020

(65) Prior Publication Data

US 2021/0055568 A1 Feb. 25, 2021

(30) Foreign Application Priority Data

Aug. 22, 2019 (JP) .................................. 2019-151777

(51) Int. Cl.
| | | |
|---|---|---|
| G02B 27/10 | (2006.01) | |
| G02B 27/12 | (2006.01) | |
| A61B 1/00 | (2006.01) | |
| A61B 1/04 | (2006.01) | |
| A61B 1/06 | (2006.01) | |

(52) U.S. Cl.
CPC ...... *G02B 27/1013* (2013.01); *A61B 1/00009* (2013.01); *A61B 1/046* (2022.02); *A61B 1/0655* (2022.02); *G02B 27/126* (2013.01)

(58) Field of Classification Search
CPC ............ A61B 1/00009; A61B 1/00078; A61B 1/00114; A61B 1/00186; A61B 1/042; A61B 1/045; G02B 27/1006; G02B 27/1013; H04N 5/347; H04N 5/349; H04N 5/3532; H04N 9/0451; H04N 9/09

See application file for complete search history.

(56) References Cited

U.S. PATENT DOCUMENTS

| | | | | |
|---|---|---|---|---|
| 7,298,478 | B2* | 11/2007 | Gilbert | ............... G01N 21/6452 |
| | | | | 356/338 |
| 10,650,924 | B2 | 5/2020 | Kashima et al. | |
| 11,107,571 | B2 | 8/2021 | Kashima et al. | |
| 2008/0188758 | A1* | 8/2008 | Campbell | ............. G01J 3/2803 |
| | | | | 600/476 |

(Continued)

FOREIGN PATENT DOCUMENTS

| | | |
|---|---|---|
| JP | 2005-198794 A | 7/2005 |
| JP | 2014-076375 A | 5/2014 |
| JP | 2014-524290 A | 9/2014 |

(Continued)

OTHER PUBLICATIONS

U.S. Appl. No. 16/987,600, filed Aug. 7, 2020 (First Named Inventor: Junya Fukumoto).

(Continued)

Primary Examiner — Joseph P Martinez
Assistant Examiner — Vipin Patel
(74) Attorney, Agent, or Firm — Venable LLP (57) ABSTRACT

An imaging apparatus includes an optical element configured to separate incident light into light components in at least two types of wavelength bands. The incident light includes light emitted from a narrow-band light source. At least one light component of the light components in the at least two types of wavelength bands separated by the optical element is light in a narrow band separated by a bandwidth corresponding to a width of a wavelength of the light emitted from the narrow-band light source.

7 Claims, 4 Drawing Sheets (56) References Cited

U.S. PATENT DOCUMENTS

2014/0347629 A1* 11/2014 Donitzky .............. A61B 3/113
351/209
2017/0020627 A1* 1/2017 Tesar ................... A61B 90/361

FOREIGN PATENT DOCUMENTS

| JP | 2017-221486 A | 12/2017 |
| JP | 2018-175871 A | 11/2018 |
| WO | 2013/025530 A1 | 2/2013 |

OTHER PUBLICATIONS

U.S. Appl. No. 16/988,898, filed Aug. 10, 2020 (First Named Inventor: Junya Fukumoto).

Office Action dated Apr. 17, 2023, in Japanese Patent Application No. 2019-151777.

* cited by examiner

IMAGING APPARATUS

BACKGROUND OF THE INVENTION

Field of the Invention

The present disclosure relates to an imaging apparatus.

Description of the Related Art

An imaging apparatus, for example, an endoscopic apparatus has conventionally mainly used a CCD (Charge Coupled Apparatus) image sensor. Recently, however, a CMOS (Complementary Metal Oxide Semiconductor) image senor is mainly used because of its advantages such as low cost, single power supply, and low power consumption. As the CMOS image sensor, a rolling shutter method is often employed in general (see Japanese Patent Laid-Open No. 2018-175871).

SUMMARY OF THE INVENTION

One of problems to be solved by an embodiment disclosed in this specification is to ensure image quality sufficiently for observation. However, the problem is not limited to this, and obtaining functions and effects derived by configurations shown in an embodiment configured to implement the present invention to be described later can also be defined as another problem to be solved by the embodiment disclosed in this specification and the like.

An imaging apparatus according to an embodiment is an imaging apparatus comprising, an optical element configured to separate incident light into light components in at least two types of wavelength bands, wherein the incident light includes light emitted from a narrow-band light source, and wherein at least one light component of the light components in the at least two types of wavelength bands separated by the optical element is light in a narrow band separated by a bandwidth corresponding to a width of a wavelength of the light emitted from the narrow-band light source.

Further features of the present invention will become apparent from the following description of exemplary embodiments (with reference to the attached drawings).

DESCRIPTION OF THE EMBODIMENTS

An imaging apparatus according to an embodiment will now be described with reference to the accompanying drawings. Note that the embodiment is not limited to the following contents. In addition, the contents described in one embodiment or modification are similarly applied to another embodiment or modification in principle.

Figure 1:
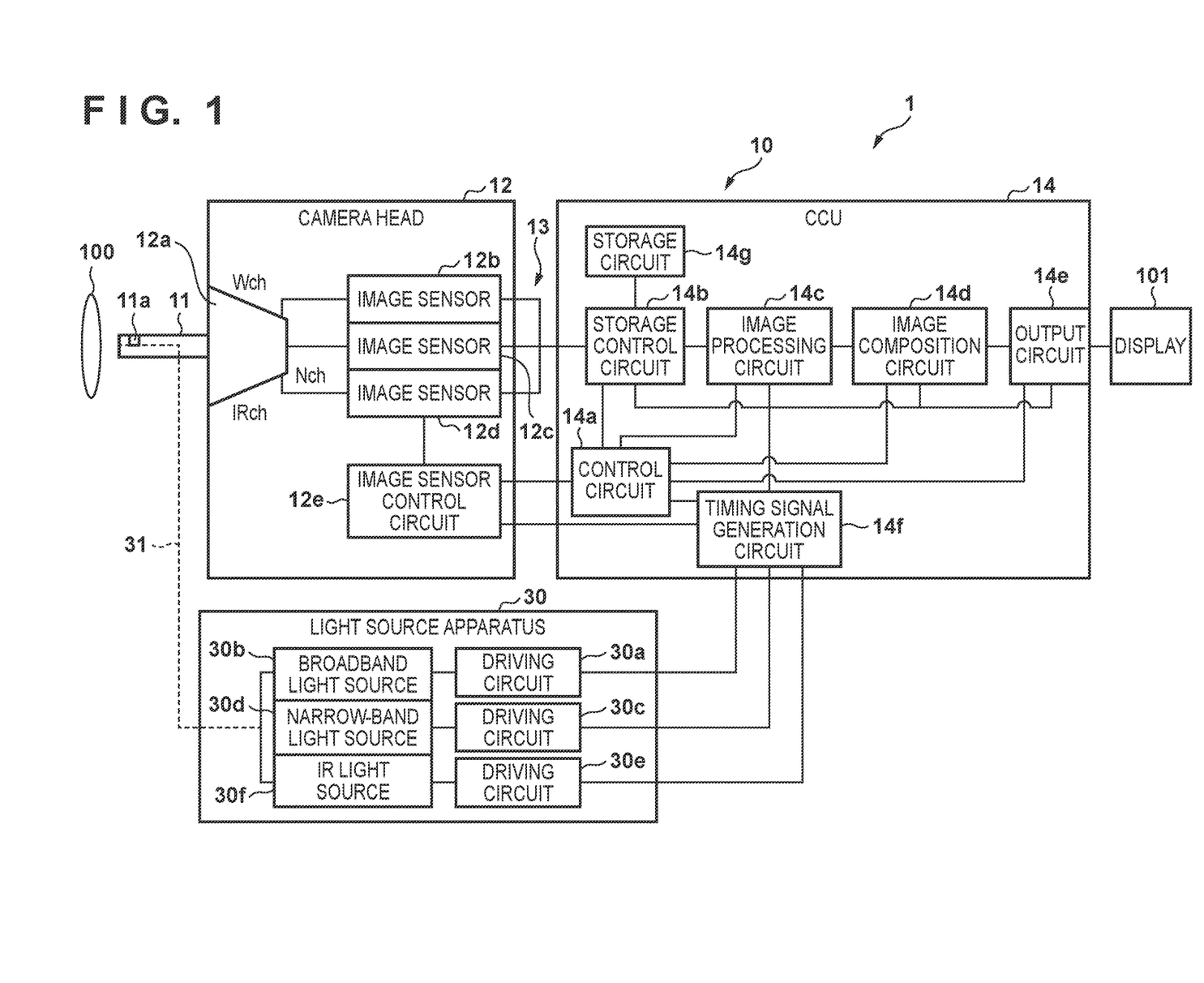
FIG. 1 is a block diagram showing an example of the configuration of an imaging system including an imaging apparatus according to an embodiment.

FIG. 1 is a block diagram showing an example of the configuration of an imaging system 1 including an imaging apparatus 10 according to this embodiment. As shown in FIG. 1, the imaging system 1 according to this embodiment includes the imaging apparatus 10, a light source apparatus 30, and an optical fiber 31.

The imaging apparatus 10 is used as, for example, a rigid endoscope for a medical application, which is an apparatus that captures the inside of a subject 100. The imaging apparatus 10 includes a scope 11, a camera head 12, a camera cable 13, and a CCU (Camera Control Unit) 14. Note that the imaging apparatus 10 is not limited only to the rigid endoscope.

The scope 11 is inserted into the inside of the subject 100 when performing imaging. An objective lens 11a is provided at the distal end of the scope 11.

The camera head 12 includes a prism 12a, a plurality of image sensors 12b, 12c, and 12d, and an image sensor control circuit 12e.

The prism 12a separates incident light into light components in two or more types of wavelength bands. For example, the prism 12a spectrally divides incident light into light in a narrow band and light in a wavelength band other than the wavelength band of the light in the narrow band. More specifically, the prism 12a spectrally divides incident light into light in a narrow band, light in a broadband, and light in an infrared wavelength band. The broadband is a wavelength band wider than the narrow band, and light in the broadband is light in a visible light band other than the wavelength band of the light in the narrow band. The prism 12a is an example of an optical element.

The plurality of image sensors receive the light components in the two or more types of wavelength bands separated by the prism 12a, respectively. For example, the plurality of image sensors are CMOS (Complementary Metal Oxide Semiconductor) image sensors. For example, as the plurality of image sensors, the image sensors 12b, 12c, and 12d receive the light in the broadband, the light in the narrow band, and the light in the infrared wavelength band separated by the prism 12a, respectively. The image sensor 12b corresponds to, for example, the broadband (expressed as "Wch (channel)" in FIG. 1), and is provided on the exit surface of the prism 12a for spectrally divided light in the broadband. The image sensor 12c corresponds to, for example, the narrow band (expressed as "Nch" in FIG. 1), and is provided on the exit surface of the prism 12a for spectrally divided light in the narrow band. The image sensor 12d corresponds to, for example, the infrared wavelength band (expressed as "IRch" in FIG. 1), and is provided on the exit surface of the prism 12a for spectrally divided light in the infrared wavelength band. The image sensors 12b, 12c, and 12d will sometime be referred to as the image sensor 12b on the Wch side, the image sensor 12c on the Nch side, and the image sensor 12d on the IRch side, respectively, hereinafter. The imaging surfaces of the image sensors 12b, 12c, and 12d are arranged to almost match the imaging surface of an optical system including the scope 11. The image sensors 12b, 12c, and 12d are examples of an imaging element.

Each of the image sensors 12b, 12c, and 12d includes a plurality of pixels (imaging pixels). The plurality of pixels are arranged in a matrix on the imaging surface. Under the driving control of the image sensor control circuit 12e, each pixel generates a video signal (electrical signal) by receiving light, and outputs the generated video signal. More specifically, for example, the image sensor 12*b* is a color sensor, and each pixel of the image sensor 12*b* receives light in the broadband, thereby outputting a video signal of a broadband image that is an RGB image. For example, the image sensor 12*c* is a monochrome sensor, and each pixel of the image sensor 12*c* receives light in the narrow band, thereby outputting a video signal of a narrow-band image. For example, the image sensor 12*d* is a monochrome sensor, and each pixel of the image sensor 12*d* receives light in the infrared wavelength band, thereby outputting a video signal of an IR image. For example, the camera head 12 including the image sensors 12*b*, 12*c*, and 12*d* outputs an RGB signal to the CCU 14 via the camera cable 13. Note that an analog video signal is output from each of the image sensors 12*b*, 12*c*, and 12*d*. Alternatively, if each of the image sensors 12*b*, 12*c*, and 12*d* incorporates an A/D (Analog to Digital) converter (not shown), a digital video signal is output from each of the image sensors 12*b*, 12*c*, and 12*d*.

Here, the imaging apparatus 10 according to this embodiment is used when, for example, performing a surgical operation by ICG (IndoCyanine Green) fluorescence angiography for the subject 100. In this case, ICG is administered to the subject 100. ICG is excited by excitation light emitted by an IR laser 30*d* and emits near-infrared fluorescence (to be referred to as fluorescence hereinafter) of about 800 to 850 nm. In the ICG fluorescence angiography, a filter that cuts excitation light is provided between the scope 11 and the prism 12*a*, and the fluorescence is received by the image sensor 12*d*. That is, the image sensor 12*d* receives the fluorescence based on the excitation light, thereby outputting a video signal of an IR image.

Each of the image sensors 12*b*, 12*c*, and 12*d* is a rolling shutter image sensor that repeats, for every frame (image), processing of sequentially starting exposure, at least on each row, from the first row to the final row of the plurality of pixels and outputting a video signal sequentially from a row that has undergone the exposure. Here, exposure means, for example, accumulating charges in the pixels.

The image sensor control circuit 12*e* drives and controls the image sensors 12*b*, 12*c*, and 12*d* based on a control signal output from a control circuit 14*a* to be described later and various kinds of synchronization signals output from a timing signal generation circuit 14*f* to be described later. For example, if the image sensors 12*b*, 12*c*, and 12*d* output analog video signals, the image sensor control circuit 12*e* appropriately applies a gain (analog gain) to each of the analog video signals output from the image sensors 12*b*, 12*c*, and 12*d* (amplifies the video signals) based on the control signal and the various kinds of synchronization signals, thereby controlling the image sensors 12*b*, 12*c*, and 12*d* such that the video signals multiplied by the gain are output to the CCU 14. Alternatively, if the image sensors 12*b*, 12*c*, and 12*d* output digital video signals, the image sensor control circuit 12*e* appropriately applies a gain (digital gain) to each of the digital video signals output from the image sensors 12*b*, 12*c*, and 12*d* based on the control signal and the various kinds of synchronization signals, thereby controlling the image sensors 12*b*, 12*c*, and 12*d* such that the video signals multiplied by the gain are output to the CCU 14.

The camera cable 13 is a cable that stores signal lines configured to transmit/receive video signals, control signals, and synchronization signals between the camera head 12 and the CCU 14.

The CCU 14 performs various kinds of image processing for a video signal output from the camera head 12 to generate image data to be displayed on a display 101, and outputs the image data to the display 101 connected to the CCU 14. Note that the video signal that has undergone the various kinds of image processing is image data representing an image to be displayed on the display 101.

The CCU 14 includes the control circuit 14*a*, a storage control circuit 14*b*, an image processing circuit 14*c*, an image composition circuit 14*d*, an output circuit 14*e*, the timing signal generation circuit 14*f*, and a storage circuit 14*g*. Note that when the image sensors 12*b*, 12*c*, and 12*d* output analog video signals, the CCU 14 includes an A/D converter and the like (not shown) as well. The A/D converter converts, for example, analog video signals output from the image sensors 12*b*, 12*c*, and 12*d* into digital video signals.

The control circuit 14*a* controls various kinds of constituent elements of the imaging apparatus 10. For example, the control circuit 14*a* outputs control signals to the image sensor control circuit 12*e*, the storage control circuit 14*b*, the image processing circuit 14*c*, the image composition circuit 14*d*, the output circuit 14*e*, and the timing signal generation circuit 14*f*, thereby controlling the circuits. The control circuit 14*a* loads the control program of the imaging apparatus 10, which is stored in the storage circuit 14*g*, and executes the loaded control program, thereby executing control processing of controlling the various kinds of constituent elements of the imaging apparatus 10. Alternatively, the control circuit 14*a* incorporates a storage circuit (not shown) and executes a control program stored in the storage circuit. The control circuit 14*a* is implemented by, for example, a processor such as an MPU (Micro-Processing Unit).

The storage control circuit 14*b* performs control of storing, in the storage circuit 14*g*, a video signal output from the camera head 12 based on a control signal output from the control circuit 14*a* and various kinds of synchronization signals output from the timing signal generation circuit 14*f*. In addition, the storage control circuit 14*b* reads the video signal stored in the storage circuit 14*g* from each row based on the control signal and the synchronization signals. The storage control circuit 14*b* then outputs the read video signal of one row to the image processing circuit 14*c*.

The image processing circuit 14*c* performs various kinds of image processing for the video signal output from the storage control circuit 14*b* based on a control signal output from the control circuit 14*a* and various kinds of synchronization signals output from the timing signal generation circuit 14*f*. The image processing circuit 14*c* thus generates image data representing an image to be displayed on the display 101. That is, the image processing circuit 14*c* generates the image based on the video signal. For example, the image processing circuit 14*c* applies a gain (digital gain) to the video signal output from the storage control circuit 14*b*, thereby adjusting the brightness of the image. The image processing circuit 14*c* may perform noise reduction processing of reducing noise or edge enhancement processing of enhancing edges for the video signal output from the storage control circuit 14*b*. The image processing circuit 14*c* outputs the video signal (image data representing the image to be displayed on the display 101) that has undergone the various kinds of image processing to the image composition circuit 14*d*.

The image composition circuit 14*d* composites video signals output from the image processing circuit 14*c* to generate composite image data based on a control signal output from the control circuit 14*a* and various kinds of synchronization signals output from the timing signal generation circuit 14*f*. The image composition circuit 14*d* outputs the composite image data to the display 101. The image processing circuit 14c and the image composition circuit 14d are examples of processing units.

For example, the storage control circuit 14b, the image processing circuit 14c, and the image composition circuit 14d are implemented by one processor such as a DSP (Digital Signal Processor). Alternatively, for example, the storage control circuit 14b, the image processing circuit 14c, the image composition circuit 14d, and the timing signal generation circuit 14f are implemented by one FPGA (Field Programmable Gate Array). Note that the control circuit 14a, the storage control circuit 14b, the image processing circuit 14c, and the image composition circuit 14d may be implemented by one processing circuit. The processing circuit is implemented by, for example, a processor.

The output circuit 14e outputs the composite image data output from the image composition circuit 14d to the display 101. The display 101 thus displays a composite image represented by the composite image data. The composite image is an example of an image. The output circuit 14e is implemented by, for example, an HDMI® (High-Definition Multimedia Interface) driver IC (Integrated Circuit), an SDI (Serial Digital Interface) driver IC, or the like.

The timing signal generation circuit 14f unitarily manages various kinds of timings such as the emission timing of light from the light source apparatus 30, the exposure timings and video signal output timings of the image sensors 12b, 12c, and 12d, and the control timing of the storage circuit 14g by the storage control circuit 14b.

The timing signal generation circuit 14f generates various kinds of synchronization signals such as a horizontal synchronization signal and a vertical synchronization signal, and other synchronization signals used to synchronize the entire imaging apparatus 10 based on a clock signal generated by an oscillation circuit (not shown). The timing signal generation circuit 14f outputs the generated various kinds of synchronization signals to the image sensor control circuit 12e, the control circuit 14a, the storage control circuit 14b, the image processing circuit 14c, the image composition circuit 14d, and the output circuit 14e.

In addition, the timing signal generation circuit 14f generates a light source control signal based on the clock signal and a control signal output from the control circuit 14a. The light source control signal is a control signal used to control light emitted from the light source apparatus 30 and also synchronize the entire imaging system 1. The timing signal generation circuit 14f outputs the generated light source control signal to the light source apparatus 30.

For example, the light source control signal has a rectangular waveform, and takes two levels (states), that is, high level and low level. For example, the light source control signal is a control signal that causes the light source apparatus 30 to emit light during high level, and stops emission of light from the light source apparatus 30 during low level.

The storage circuit 14g is implemented by, for example, a RAM (Random Access Memory), a ROM (Read Only Memory), a semiconductor memory element such as a flash memory, a hard disk, an optical disk, or the like. The ROM (or flash memory or hard disk) stores various kinds of programs. For example, the ROM stores a control program to be executed by the control circuit 14a. In addition, video signals are temporarily stored in the RAM by the storage control circuit 14b.

The light source apparatus 30 emits various kinds of light based on the light source control signal. The light source apparatus 30 includes a driving circuit 30a, a broadband light source 30b, a driving circuit 30c, a narrow-band light source 30d, a driving circuit 30e, and an IR light source 30f.

The driving circuit 30a performs driving control of driving and turning on the broadband light source 30b based on the light source control signal output from the timing signal generation circuit 14f. The broadband light source 30b is, for example, a white LED (Light Emitting Diode), and emits white light as light in the broadband under the driving control of the driving circuit 30a. The white light is, for example, visible light. Note that the light in the broadband is separated by the prism 12a and received by the image sensor 12b.

The driving circuit 30c performs driving control of driving and turning on the narrow-band light source 30d based on the light source control signal output from the timing signal generation circuit 14f. The narrow-band light source 30d is, for example, a blue LED or a blue laser, and emits blue light as light in the narrow band under the driving control of the driving circuit 30c. The blue light is, for example, visible light. Note that the light in the narrow band is separated by the prism 12a and received by the image sensor 12c.

The driving circuit 30e performs driving control of driving the IR light source 30f to cause the IR light source 30f to emit excitation light based on the light source control signal output from the timing signal generation circuit 14f. The IR light source 30f is, for example, an IR laser, and emits excitation light under the driving control of the driving circuit 30e. Note that ICG is excited by the excitation light, and fluorescence (fluorescence based on the excitation light) emitted from the ICG is separated by the prism 12a and received by the image sensor 12d.

The optical fiber 31 guides the various kinds of light from the light source apparatus 30 to the distal end portion of the scope 11 and outputs the light from the distal end portion of the scope 11.

An example of the configuration of the imaging apparatus 10 of the imaging system 1 according to this embodiment has been described above. An imaging apparatus according to a comparative example will be described here. The imaging apparatus according to the comparative example is a general imaging apparatus. For example, the imaging apparatus according to the comparative example does not have the functions of the narrow-band light source 30d, the driving circuit 30c, and the like, and includes a prism 112a and image sensors 112b, 112c, and 112d shown in FIG. 2 in place of the above-described prism 12a and the image sensors 12b, 12c, and 12d. For example, the prism 112a is a tricolor separating dichroic prism, and the image sensors 112b, 112c, and 112d are monochrome sensors. In the imaging apparatus according to the comparative example, when white light is emitted, the image sensors 112b, 112c, and 112d receive red (R+IR) light, green (G) light, and blue (B) light separated by the prism 112a, and output an R signal (video signal of R), a G signal (video signal of G), and a B signal (video signal of B), respectively. Hence, the imaging apparatus according to the comparative example can acquire an RGB image based on the R signal, the G signal, and the B signal (RGB signal).

Figure 2:
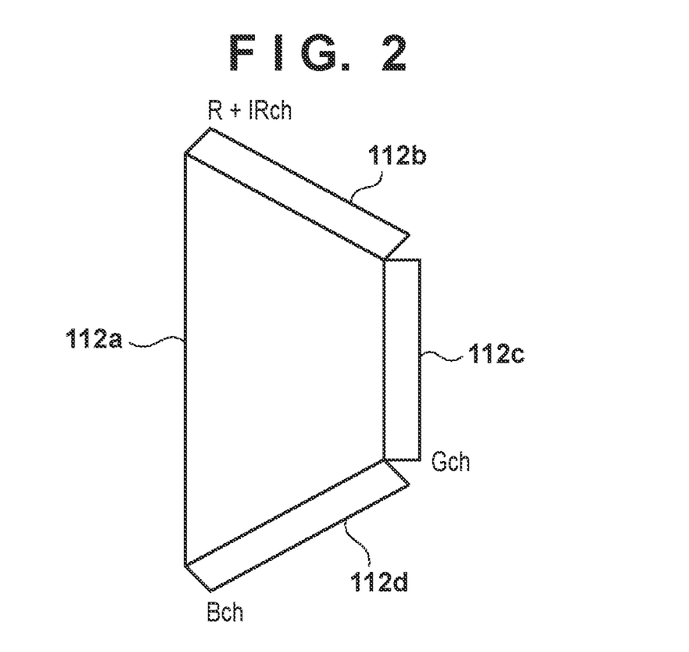
FIG. 2 is a view showing some components of an imaging apparatus according to a comparative example.

As described above, in the imaging apparatus according to the comparative example, the imaging target is irradiated with light in the broadband such as white light, and the image sensors 112b, 112c, and 112d receive the light in the broadband separated by the prism 112a, thereby acquiring an RGB image. Since the emitted white light is light in the broadband from the blue wavelength band to the infrared wavelength band beyond the red wavelength band, the acquired image includes the color components of the imaging target. For this reason, the imaging apparatus according to the comparative example can correctly reproduce the color of the imaging target. However, the reflection and scattering characteristics of light change depending on the wavelength. For example, the reflection and scattering characteristics of light change between the red wavelength band, the green wavelength band, and the blue wavelength band. Hence, when an image is acquired by emitting light in the broadband such as white light, the resolution of the image may lower due to reflection or scattering of light. For example, concerning the contour of unevenness or the like on the surface of the imaging target, the contrast may lower due to reflection or scattering of light. Hence, for a user such as a doctor who observes images, image quality may not be sufficient for observation.

On the other hand, there exists a technique of irradiating an imaging target with light in the narrow band to increase the resolution of an image. For example, if an image is acquired by irradiating an imaging target with light in the blue wavelength band as light in the narrow band using an LED or a laser, the contrast can be increased concerning the contour of unevenness or the like on the surface of the imaging target. However, if the imaging target is irradiated with light in the blue wavelength band as light in the narrow band, information concerning colors is only information of blue, and there is no information of other colors such as red and green. For this reason, if an image is acquired by irradiating the imaging target with only light in the narrow band, the color of the imaging target cannot correctly be reproduced.

The imaging apparatus 10 according to this embodiment performs the following processing to ensure image quality sufficient for the user to observe. The imaging apparatus 10 according to this embodiment includes the prism 12a. The prism 12a is an optical element that separates incident light into light components in two or more types of wavelength bands. The incident light includes light emitted from the narrow-band light source 30d. At least one light component of the light components in two or more types of wavelength bands separated by the prism 12a is light in the narrow band which is separated by a bandwidth corresponding to the width of the wavelength of light emitted from the narrow-band light source 30d.

Alternatively, the imaging apparatus 10 according to this embodiment performs the following processing to ensure image quality sufficient for the user to observe. The imaging apparatus 10 according to this embodiment includes the prism 12a, and the plurality of image sensors. The prism 12a is an optical element that separates incident light into light components in two or more types of wavelength bands. The plurality of image sensors are imaging elements that receive the light components in two or more types of wavelength bands separated by the prism 12a, respectively. At least one image sensor of the plurality of image sensors outputs an RGB image independently. For example, at least one image sensor of the plurality of image sensors outputs a narrow-band image by receiving light in the narrow band, and at least one other image sensor outputs a broadband image that is an RGB image by receiving light in the broadband that is a wavelength band wider than the narrow band. As the image sensor that receives light in the narrow band for example, a monochrome image sensor (monochrome imaging element) can be used. In addition, as the image sensor that receives light in the broadband that is a wavelength band wider than the narrow band, for example, an RGB color image sensor (color imaging element) can be used.

Figure 3:
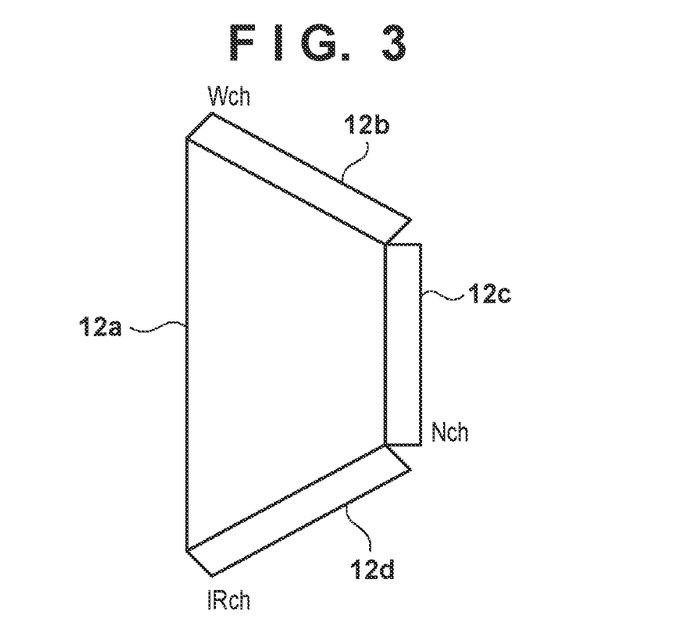
FIG. 3 is a view showing some components of the imaging apparatus according to an embodiment.

More specifically, in the imaging apparatus 10 according to this embodiment, as shown in FIG. 3, the prism 12a is a prism that spectrally divides incident light into light in the broadband, light in the narrow band, and light in the infrared wavelength band, the image sensor 12b is a color sensor, and the image sensors 12c and 12d are monochrome sensors. In the imaging apparatus 10 according to this embodiment, the image sensors 12b, 12c, and 12d receive the light in the broadband, the light in the narrow band, and the light in the infrared wavelength band separated by the prism 12a, and output a video signal of a broadband image, a video signal of a narrow-band image, and a video signal of an IR image, respectively. Accordingly, in the imaging apparatus 10 according to this embodiment, the image processing circuit 14c acquires an RGB image based on the video signal of the broadband image (RGB signal), and generates a display image based on the narrow-band image and the broadband image. The display image includes, for example, the contour component of the imaging target included in the narrow-band image, and the color component of the imaging target included in the broadband image or the composite image of the broadband image and the narrow-band image.

Figure 4:
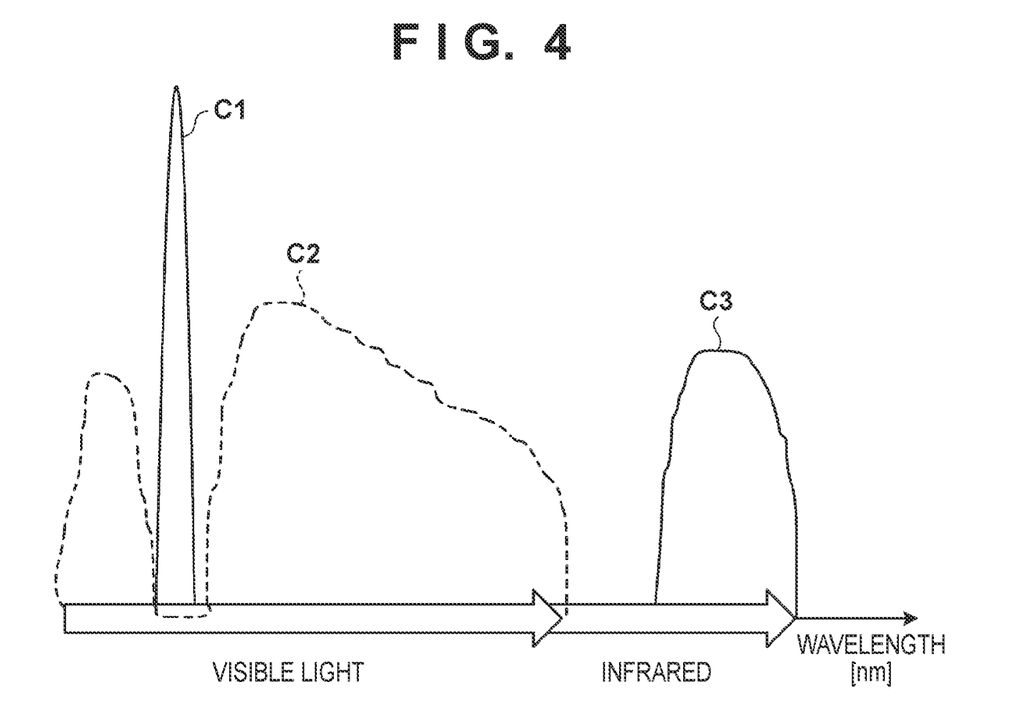
FIG. 4 is a graph for explaining processing of the imaging apparatus according to an embodiment.

FIG. 4 is a graph showing an example of the transmission characteristic (spectral transmission characteristic) of light separated by the prism 12a of the imaging apparatus 10 according to this embodiment. FIG. 4 shows an example of the relationship between the spectral transmission characteristic to light in the narrow band, the spectral transmission characteristic to light in the broadband, and the spectral transmission characteristic to light in the infrared wavelength band. In FIG. 4, the abscissa represents wavelength [nm]. Additionally, in FIG. 4, a curve C1 represents a spectral transmission characteristic to light in the narrow band, a curve C2 represents a spectral transmission characteristic to light in the broadband, and a curve C3 represents a spectral transmission characteristic to light in the infrared wavelength band.

The light in the narrow band indicated by the curve C1 is used for, for example, the contour component of the imaging target. More specifically, several spectral films are provided in the prism 12a. A wavelength transmitted through the spectral films and a reflected wavelength are guided to different optical paths, thereby spectrally dividing blue light as light in the narrow band from Nch of the prism 12a. The image sensor 12c that is a monochrome sensor receives the light in the narrow band spectrally divided by the prism 12a, and outputs a video signal of a narrow-band image. Here, the narrow-band image includes the contour component of the imaging target. Hence, the imaging apparatus 10 according to this embodiment can increase the contrast concerning the contour of unevenness or the like on the surface of the imaging target, and the resolution improves.

Here, the light in the narrow band that has exited from Nch of the prism 12a is light separated by a bandwidth (for example, a half-value width) corresponding to the width of the wavelength of light emitted from the narrow-band light source 30d, and the half-value width is set to, for example, 50 [nm] or less. Note that in this embodiment, a case in which the half-value width is set to 50 [nm] or less has been exemplified. However, the half-value width is not limited to this, and may be set within a wavelength range corresponding to the emission color of a general LED. If a laser is used, the half-value width may be set within a narrow wavelength range such as about 1 [nm] or 10 [nm]. Note that the half-value width includes a full width at half maximum and a half width at half maximum that is ½ the full width at half maximum. In this embodiment, either is usable.

The light in the broadband indicated by the curve C2 is used for, for example, the color component of the imaging target. More specifically, light in the broadband is spectrally divided from Wch of the prism 12*a*. The image sensor 12*b* that is a color sensor receives the light in the broadband spectrally divided by the prism 12*a*, and outputs a video signal of a broadband image. Here, as shown in FIG. 4, if the light in the broadband indicated by the curve C2 is light in a visible band other than the wavelength band of the light in the narrow band indicated by the curve C1, the broadband image or the composite image of the broadband image and the narrow-band image includes the color component of the imaging target. Hence, the imaging apparatus 10 according to this embodiment can correctly reproduce the color of the imaging target.

Note that the light in the infrared wavelength band indicated by the curve C3 is used to, for example, generate a fluorescent image to be described later. More specifically, light in the infrared wavelength band is spectrally divided from IRch of the prism 12*a*. The image sensor 12*d* that is a monochrome sensor receives the light in the infrared wavelength band spectrally divided by the prism 12*a*, and outputs a video signal of an IR image. Here, a portion with a brightness equal to or larger than a threshold exists in the IR image, and the fluorescent image to be described later is generated based on this portion.

Figure 5:
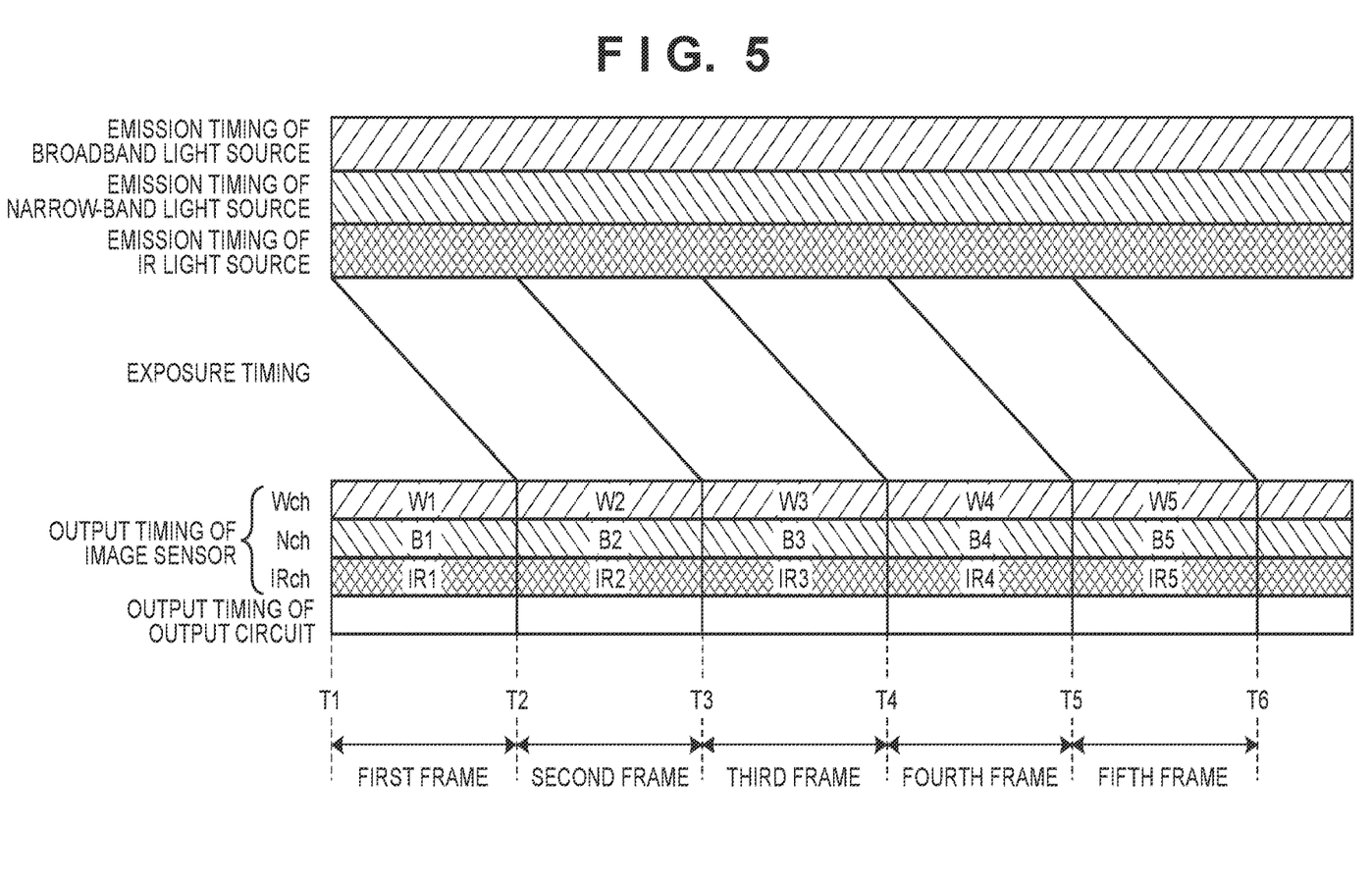
FIG. 5 is a view showing an example of an imaging operation of the imaging apparatus according to an embodiment.

FIG. 5 is a view showing an example of an imaging operation of the imaging apparatus 10 according to this embodiment. FIG. 5 shows an example of the relationship between the emission timings of white light, blue light, and excitation light emitted from the light source apparatus 30, the exposure timings of the rows of the plurality of pixels provided in the image sensors 12*b*, 12*c*, and 12*d* of the imaging apparatus 10, the output timings of video signals output from the image sensors 12*b*, 12*c*, and 12*d*, and the output timings of a video signal output from the output circuit 14*e*. In FIG. 5, the abscissa represents time. In this embodiment, the frame rate of a video signal (image) output from the imaging apparatus 10 to the display 101 is 60 [fps], and the read period is ⅟60 [s]. That is, the period of outputting a video signal of one frame from the imaging apparatus 10 to the display 101 and the read period are ⅟60 [s].

First, at the start of imaging, the control circuit 14*a* outputs a control signal to the timing signal generation circuit 14*f* to cause it to output a first light source control signal that causes the broadband light source 30*b* to continuously emit white light. The timing signal generation circuit 14*f* outputs the first light source control signal to the driving circuit 30*a* based on the control signal, and the driving circuit 30*a* drives the broadband light source 30*b* based on the first light source control signal, thereby causing the broadband light source 30*b* to continuously emit white light.

Also, at the start of imaging, the control circuit 14*a* outputs a control signal to the timing signal generation circuit 14*f* to cause it to output a second light source control signal that causes the narrow-band light source 30*d* to continuously emit blue light. The timing signal generation circuit 14*f* outputs the second light source control signal to the driving circuit 30*c* based on the control signal, and the driving circuit 30*c* drives the narrow-band light source 30*d* based on the second light source control signal, thereby causing the narrow-band light source 30*d* to continuously emit blue light.

Additionally, at the start of imaging, the control circuit 14*a* outputs a control signal to the timing signal generation circuit 14*f* to cause it to output a third light source control signal that causes the IR light source 30*f* to continuously emit excitation light. The timing signal generation circuit 14*f* outputs the third light source control signal to the driving circuit 30*e* based on the control signal, and the driving circuit 30*e* drives the IR light source 30*f* based on the third light source control signal, thereby causing the IR light source 30*f* to continuously emit excitation light.

For example, in the first frame, during the read period of ⅟60 [s] from time T1 to time T2, exposure is sequentially started on each row from the first row to the final row of the plurality of pixels of each of the image sensors 12*b*, 12*c*, and 12*d*. More specifically, the control circuit 14*a* outputs a control signal to the image sensor control circuit 12*e* to cause each of the image sensors 12*b*, 12*c*, and 12*d* to output a video signal during the read period of ⅟60 [s]. The image sensor control circuit 12*e* drives and controls the image sensors 12*b*, 12*c*, and 12*d* based on the control signal. As a result, during the read period of ⅟60 [s], the image sensor 12*b* receives light in the broadband and outputs video signals from all rows as a video signal "W1" of a broadband image. The image sensor 12*c* receives light in the narrow band and outputs video signals from all rows as a video signal "B1" of a narrow-band image. The image sensor 12*d* receives light in the infrared wavelength band and outputs video signals from all rows as a video signal "IR1" of an IR image. In this case, the video signal "W1" of the broadband image, the video signal "B1" of the narrow-band image, and the video signal "IR1" of the IR image are output from the image sensors 12*b*, 12*c*, and 12*d*, respectively. The video signal "W1" of the broadband image is a signal output from the image sensor 12*b* that has received the white light. The video signal "B1" of the narrow-band image is a signal output from the image sensor 12*c* that has received the blue light. The video signal "IR1" of the IR image is a signal output from the image sensor 12*d* that has received fluorescence based on the excitation light.

Next, in the second frame, during the read period of ⅟60 [s] from time T2 to time T3, the image sensors 12*b*, 12*c*, and 12*d* output video signals as a video signal "W2" of a broadband image, a video signal "B2" of a narrow-band image, and a video signal "IR2" of an IR image, respectively. In this case, the video signal "W2" of the broadband image, the video signal "B2" of the narrow-band image, and the video signal "IR2" of the IR image are output from the image sensors 12*b*, 12*c*, and 12*d*, respectively.

Here, the video signals output from the image sensors 12*b*, 12*c*, and 12*d* are changed to the display image of the first frame via the image processing circuit 14*c* and the image composition circuit 14*d* in the CCU 14, and quickly output from the output circuit 14*e* to the display 101. More specifically, the image processing circuit 14*c* generates a first display image based on the broadband image represented by the video signal "W1" and the narrow-band image represented by the video signal "B1". The first display image includes, for example, the resolution component of the imaging target included in the narrow-band image, and the color component of the imaging target included in the broadband image or the composite image of the broadband image and the narrow-band image. Next, the image composition circuit 14*d* extracts, as a target, a portion with a brightness equal to or larger than a threshold from, for example, the IR image represented by the video signal "IR1", and generates a fluorescent image that is a marker formed by adding a fluorescent color to the extracted portion. The fluorescent color is a color assigned to represent fluorescence when the marker (fluorescent image) is generated, and shows, for example, green of high saturation. The image composition circuit 14*d* superimposes the generated fluorescent image on the first display image generated by the image processing circuit 14*c*, thereby generating a second display image. The second display image generated by the image composition circuit 14*d* is output from the output circuit 14*e* to the display 101 during the period of 1/60 [s]. From the second frame as well, processing similar to the above-described processing is performed.

Note that in this embodiment, as the first display image generated by the image processing circuit 14*c*, the video signal of the first display image represents the composite signal of the video signal "W1" of the broadband image and the video signal "B1" of the narrow-band image. Here, if the video signal "W1" of the broadband image (color image) is simply defined as the color image W1, and the video signal "B1" of the narrow-band image is simply defined as the narrow-band image B1, composition of the color image W1 and the narrow-band image B1 is as follows. First, a contour image D1 is generated based on the narrow-band image B1. The contour image D1 is a signal having a positive/negative value whose average value is 0. For example, the contour image D1 is obtained by extracting a frequency component more than a certain frequency band from the narrow-band image B1 using a high-frequency extraction filter (HPF). The composite formula at this time is represented by W1+D1×K. A coefficient K represents the strength of a contour. The larger the coefficient K is, the stronger the contour of the color image is. For example, the coefficient K may be arbitrarily adjustable by the user.

As described above, in the imaging apparatus 10 according to this embodiment, the imaging target is irradiated with light in the blue wavelength band as light in the narrow band, and the image sensor 12*c* receives the light in the narrow band separated by the prism 12*a*, thereby acquiring the narrow-band image. Also, in the imaging apparatus 10, the imaging target is irradiated with light in the broadband such as white light, and the image sensor 12*b* receives the light in the broadband separated by the prism 12*a*, thereby acquiring the broadband image (RGB image). Furthermore, in the CCU 14, the display image is generated based on the narrow-band image and the broadband image. Here, the display image includes the contour component of the imaging target included in the narrow-band image. For this reason, according to the imaging apparatus 10 of this embodiment, it is possible to increase contrast concerning the contour of unevenness or the like on the surface of the imaging target, and the resolution improves. In addition, the display image includes the color component of the imaging target included in the broadband image or the composite image of the broadband image and the narrow-band image. For this reason, according to the imaging apparatus 10 of this embodiment, it is possible to correctly reproduce the color of the imaging target. Hence, in this embodiment, image quality sufficient for the user to observe can be ensured.

The imaging apparatus 10 according to this embodiment includes the prism 12*a* that separates incident light into light components in two or more types of wavelength bands. More specifically, the imaging apparatus 10 according to this embodiment uses the prism 12*a* that spectrally divides incident light into light in the narrow band and light in the broadband. Hence, in this embodiment, for example, in the camera head 12, the prism 112*a* (tricolor separating dichroic prism) according to the comparative example need only be changed to the prism 12*a*, and it is possible to implement circuits and apparatuses of a scale similar to the comparative example.

The reason why light in the blue wavelength band is selected as light in the narrow band in this embodiment will be described here using an examination result.

It is generally known that when an image is acquired using light in the blue wavelength band, the contrast is high concerning unevenness on the surface of the imaging target. It is also known that when an image is acquired using light in the red wavelength band, the contrast is low because of large transmission or scattering of the red component. Contrast and the like were actually examined using the prism 112*a* shown in FIG. 2. More specifically, a "palm" was used as an imaging target, and contrast and the like were examined in a case where a filter configured to pass light in the red wavelength band was arranged in front of the incident surface of the prism 112*a* shown in FIG. 2, and images were acquired from R+IRch of the prism 112*a* and in a case where images were acquired from R+IRch of the prism 112*a* without arranging the filter. Similarly, contrast and the like were examined in a case where a filter configured to pass light in the green wavelength band was arranged in front of the incident surface of the prism 112*a*, and images were acquired from Gch of the prism 112*a* and in a case where images were acquired from Gch of the prism 112*a* without arranging the filter. Similarly, contrast and the like were examined in a case where a filter configured to pass light in the blue wavelength band was arranged in front of the incident surface of the prism 112*a*, and images were acquired from Bch of the prism 112*a* and in a case where images were acquired from Bch of the prism 112*a* without arranging the filter.

As the result of examinations, as for, for example, the tint of the surface of the "palm" (for example, shades or tones of colors by blood vessels or the like), it was confirmed that images acquired using light in the green wavelength band were more easily visible than images acquired using light in the red or blue wavelength band. As for unevenness on the surface of the "palm", it was confirmed that images acquired using light in the blue wavelength band had higher contrast than images acquired using light in the red or green wavelength band. Also, as a result of narrowing the wavelength band, it was confirmed that contrast improved in all of images acquired using light in the red wavelength band, images acquired using light in the green wavelength band, and images acquired using light in the blue wavelength band. At this time, in a case where light in the red wavelength band was used, a bandpass filter having a center wavelength of 607 [nm] and a half-value width of 42 [nm] was used as the filter arranged in front of the incident surface of the prism 112*a*. In a case where light in the green wavelength band was used, a bandpass filter having a center wavelength of 534.5 [nm] and a half-value width of 48 [nm] was used. In a case where light in the blue wavelength band was used, a bandpass filter having a center wavelength and a half-value width of 35 [nm] was used. Hence, the transmission characteristics (half-value widths) of the filters were almost 50 [nm] or less.

Hence, in this embodiment, Nch is assigned to the prism 12*a* shown in FIGS. 1 and 3 to improve the contrast, and light in the blue wavelength band of the highest contrast is selected as the light in the narrow band. That is, in the imaging apparatus 10 according to this embodiment, as an example, the imaging target is irradiated with light in the blue wavelength band as light in the narrow band, and the image sensor 12*c* receives the light in the narrow band separated by the prism 12*a* to acquire a narrow-band image, thereby improving the contrast.

Note that in this embodiment, a case in which the prism 12a that spectrally divides incident light into light in the broadband, light in the narrow band, and light in the infrared wavelength band is used as the optical element that spectrally divides incident light into light components in two or more types of wavelength bands has been described. That is, a case in which Wch, Nch, and IRch are assigned to the prism 12a, as shown in FIGS. 1 and 3 has been described. However, the optical element described in the embodiment is not limited to this. For example, if it is possible to improve contrast and correctly reproduce the color of the imaging target by the configuration of this embodiment, the prism 12a that spectrally divides incident light into light in the broadband and light in the narrow band may be used as the optical element that spectrally divides incident light into light components in two or more types of wavelength bands. That is, only Wch and Nch may be assigned to the prism 12a without assigning IRch.

According to at least one embodiment described above, it is possible to ensure image quality sufficiently for the user to observe.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-151777, filed Aug. 22, 2019, which is hereby incorporated by reference herein in its entirety.

What is claimed is:

1. An imaging apparatus comprising:
an optical element configured to separate incident light into light components in at least two types of wavelength bands; and
a plurality of imaging elements configured to receive the light components in the at least two types of wavelength bands separated by the optical element, respectively,
wherein the incident light includes light emitted from a narrow-band light source,
wherein at least one light component of the light components in the at least two types of wavelength bands separated by the optical element is light in a narrow band separated by a bandwidth corresponding to a width of a wavelength of the light emitted from the narrow-band light source, and
wherein at least one imaging element of the plurality of imaging elements outputs a narrow-band image by receiving the light in the narrow band, and at least one other imaging element outputs a broadband image by receiving light in a broadband that is a wavelength band wider than the narrow band.

2. The apparatus according to claim 1, wherein the optical element separates the incident light into the light in the narrow band and light in a wavelength band other than a wavelength band of the light in the narrow band.

3. The apparatus according to claim 1, wherein the optical element separates the incident light into the light in the narrow band, light in a visible light band other than a wavelength band of the light in the narrow band, and light in an infrared wavelength band.

4. The apparatus according to claim 1, wherein of the imaging elements, the imaging element that receives the light in the narrow band is a monochrome imaging element.

5. The apparatus according to claim 1, wherein of the imaging elements, the imaging element that receives the light in the broadband is a color imaging element.

6. The apparatus according to claim 1, further comprising a processing unit configured to generate a display image based on the narrow-band image and the broadband image.

7. The apparatus according to claim 6, wherein the display image includes a contour component of an imaging target included in the narrow-band image, and a color component of the imaging target included in the broadband image or in a composite image of the broadband image and the narrow-band image.

* * * * *